(12) United States Patent
Piccioni

(10) Patent No.: US 10,514,237 B2
(45) Date of Patent: *Dec. 24, 2019

(54) PUBLIC SAFETY SMART BELT

(71) Applicant: Robert Louis Piccioni, Rowlett, TX (US)

(72) Inventor: Robert Louis Piccioni, Rowlett, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/149,057

(22) Filed: Oct. 1, 2018

(65) Prior Publication Data

US 2019/0033043 A1   Jan. 31, 2019

Related U.S. Application Data

(63) Continuation-in-part of application No. 15/831,297, filed on Dec. 4, 2017, now Pat. No. 10,112,575.
(Continued)

(51) Int. Cl.
*H04W 4/18*    (2009.01)
*F41H 13/00*   (2006.01)
(Continued)

(52) U.S. Cl.
CPC ............. *F41H 13/00* (2013.01); *A41D 1/005* (2013.01); *A41F 9/002* (2013.01); *A45F 3/005* (2013.01); *A45F 5/02* (2013.01); *A45F 5/021* (2013.01); *A61B 5/0022* (2013.01); *A61B 5/02055* (2013.01); *A61B 5/02438* (2013.01); *A61B 5/1112* (2013.01); *A61B 5/6831* (2013.01);
(Continued)

(58) Field of Classification Search
CPC ........... H04W 4/02; H04W 4/04; H04W 4/18; H04W 4/046

USPC .............. 455/402, 456.1, 456.2; 340/539.11, 340/573.1
See application file for complete search history.

(56) References Cited

U.S. PATENT DOCUMENTS 8,035,560 B1 * 10/2011 Glodz .................... G08B 21/22
                                                   342/357.71
10,046,732 B2 * 8/2018 Piccioni ................ G06F 1/1632

* cited by examiner

*Primary Examiner* — Sam Bhattacharya
(74) *Attorney, Agent, or Firm* — Wei Wei Jeang; Grable Martin Fulton PLLC

(57) ABSTRACT

A smart belt system worn by a person comprising an elongated belt configured for removably coupling a plurality of devices, a GPS component coupled to the belt configured to track the geo-location and movement of the belt, a microprocessor coupled to the belt, logic instructions executing by the microprocessor configured to monitor and regulate the activities of the plurality of devices and geo-location and movement data generated by the GPS component, a memory component configured for storing the logic instructions and accessible by the microprocessor, a wireless data communications system coupled to the belt configured to wirelessly communicate with an external data communications system and the microprocessor, a power and data bus disposed within the belt and communicatively coupled to at least one of the plurality of devices, GPS component, microprocessor, memory, wireless data communications systems, and data storage component; and a data storage component coupled to the belt and accessible by the microprocessor for storing activity data of at least one of the plurality of devices and the geo-location and movement data of the belt generated by the GPS component.

24 Claims, 12 Drawing Sheets

Related U.S. Application Data which is a continuation-in-part of application No. 15/420,066, filed on Jan. 30, 2017, now Pat. No. 9,859,938.

(60) Provisional application No. 62/289,313, filed on Jan. 31, 2016.

(51) Int. Cl.

| | | |
|---|---|---|
| H04Q 9/00 | (2006.01) | |
| H04B 1/3827 | (2015.01) | |
| G01S 19/13 | (2010.01) | |
| G01L 5/00 | (2006.01) | |
| A41F 9/00 | (2006.01) | |
| A41D 1/00 | (2018.01) | |
| A45F 5/02 | (2006.01) | |
| A61B 5/00 | (2006.01) | |
| A61B 5/0205 | (2006.01) | |
| B64C 39/02 | (2006.01) | |
| A61B 5/024 | (2006.01) | |
| H04L 12/40 | (2006.01) | |
| F41C 33/04 | (2006.01) | |
| A45F 3/00 | (2006.01) | |
| F41C 33/02 | (2006.01) | |
| H02J 50/10 | (2016.01) | |
| A61B 5/11 | (2006.01) | |
| H04W 84/18 | (2009.01) | |
| H02J 7/02 | (2016.01) | |
| A41B 1/08 | (2006.01) | |
| A41D 1/06 | (2006.01) | |
| A42B 1/00 | (2006.01) | |
| A42B 3/04 | (2006.01) | |
| A43B 3/00 | (2006.01) | |
| A61B 5/021 | (2006.01) | |
| A61B 5/08 | (2006.01) | |
| H04B 5/00 | (2006.01) | |

(52) U.S. Cl.
CPC .......... *B64C 39/024* (2013.01); *F41C 33/029* (2013.01); *F41C 33/046* (2013.01); *G01L 5/0052* (2013.01); *G01S 19/13* (2013.01); *H02J 50/10* (2016.02); *H04B 1/385* (2013.01); *H04L 12/40045* (2013.01); *H04Q 9/00* (2013.01); *A41B 1/08* (2013.01); *A41D 1/06* (2013.01); *A42B 1/006* (2013.01); *A42B 3/046* (2013.01); *A43B 3/0005* (2013.01); *A45F 2200/0516* (2013.01); *A45F 2200/0566* (2013.01); *A45F 2200/0591* (2013.01); *A61B 5/021* (2013.01); *A61B 5/0816* (2013.01); *B64C 2201/126* (2013.01); *B64C 2201/127* (2013.01); *B64C 2201/146* (2013.01); *H02J 7/025* (2013.01); *H04B 5/0037* (2013.01); *H04B 2001/3855* (2013.01); *H04Q 2209/40* (2013.01); *H04W 84/18* (2013.01)

PUBLIC SAFETY SMART BELT

RELATED APPLICATION

This patent application is a Continuation-In-Part of U.S. application Ser. No. 15/831,297 filed Dec. 4, 2017, which is a Continuation-In-Part of U.S. application Ser. No. 15/420, 066 filed Jan. 30, 2017, now U.S. Pat. No. 9,859,938, which claims the benefit of U.S. application Ser. No. 62/289,313 filed Jan. 31, 2016.

FIELD

The invention relates generally to a wearable computer device worn as a belt.

BACKGROUND

As public technology advances and additional hardware and software applications become available to public safety employees, the amount of space available on the "traditional" public safety utility belt to carry these devices has become limited. Another challenge is the ability to maintain power to these devices on a long-term basis, throughout the shift of the public safety employee. In addition, many of these devices and applications generate data, which must be captured and stored. For many applications this data must also be transferred or uploaded either immediately or at a latertime.

BRIEF DESCRIPTION OF THE DRAWINGS

A better understanding of the claimed subject matter can be obtained when the following detailed description of the disclosed embodiments is considered in conjunction with the following figures.

DETAILED DESCRIPTION

Figure 1:
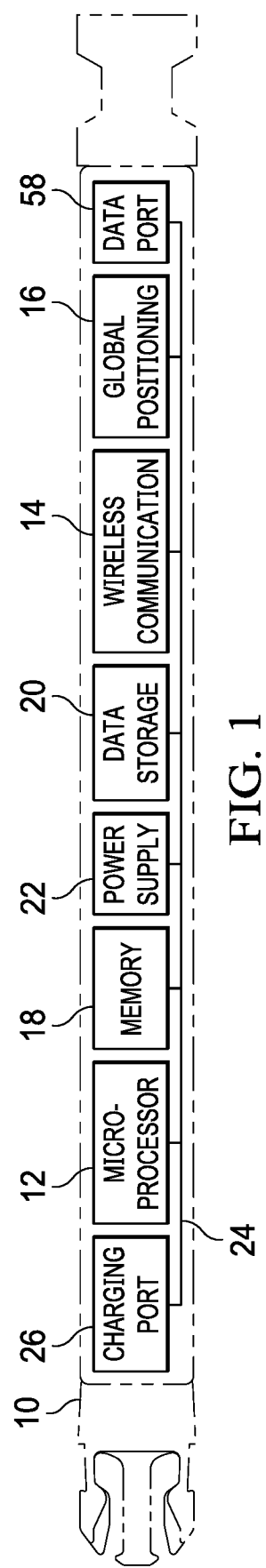
FIG. 1 is a diagram illustrating the internal components that may be wired or wirelessly connected to the smart belt according to one embodiment of the present disclosure.

Referring to FIG. 1, a wearable computer system 10, in the form of a smart belt 10 (in the form of an elongated strap and a fastener like a buckle) to be worn by a public safety employee, or other human being, to carry a myriad of tools, devices, and other items. According to one embodiment of the present disclosure, the system includes a belt 10, containing a computer microprocessor 12 that may be embedded in the belt or otherwise coupled thereto and operable to control the functions of the belt and the integration of other wired or wirelessly connected devices with the smart belt 10. The system further includes a wireless data communications system 14 disposed within or coupled to the smart belt 10 that is capable of wirelessly communicatively coupling the microprocessor 12 with external data communications systems such as cellular networks, local computer networks, and global computer networks. The smart belt 10 includes one or more radio transceiver(s) and antennae to enable wireless communication of voice data, sensor data, commands, instructions, Global Positioning System (GPS) or location data, Internet data, etc.

The smart belt 10 may contain GPS components 16 to report or record the geo-location (coordinates and/or street address) of the smart belt or its components. Here, GPS components 16 also represent accelerometer and/or gyroscope devices that are used to detect the orientation of the smart belt and generate orientation data. In addition, the smart belt 10 includes an embedded expansion area for additional memory and/or data storage devices 18. In various embodiments, memory devices 18 include one or more memory devices in various combinations, such as static memory (such as flash memory, SRAM memory and ROM devices), dynamic memory (such as RAM and DRAM). In one embodiment, memory devices are integrated within the smart belt 10 and not generally designed to be removable except for maintenance purposes. For example, in this embodiment, the smart belt 10 may be manufactured with a certain amount of memory, such as 4 GB of RAM. In another embodiment, memory devices 18 may be mounted externally or in an expandable manner, such as interfaces to receive memory modules and/or flash memory cards (such as USB, microSD and SD (Secure Digital) cards) to expand the available memory. In yet another embodiment, memory devices 18 may include a combination of both integrated memory and the functionality to allow attachment of additional memory devices coupled to the external surface(s) of the smart belt 10. In various embodiments, memory devices 18 may be used by one or more of microprocessor 12, wireless data communications system 14, GPS components 16 and devices mounted on the smart belt 12.

Further, the smart belt 10 may incorporate a removable or fixed data storage component 20 now known, such as flash memory hard drives, USB storage devices and/or rotating magnetic hard drives, or to be developed to store additional data generated by the microprocessor as well as data generated by the wired or wirelessly connected devices. Further, the smart belt 10 may contain a rechargeable power supply 22 capable of powering all of the components of the smart belt 10 as well as external components which may be integrated with the smart belt 10. The smart belt 10 may incorporate a power strip/data bus 24, disposed on the exterior or interior of the smart belt, which allows power from the power source 22 disposed within the smart belt to be transmitted to component devices that are attached to the smart belt. The power strip may also be used to provide power to the rechargeable power supply 22 and/or power the components disposed within the smart belt by attaching external power sources (power outlet, supplemental battery, etc.) via a charging port 26 to transfer the power. In addition, the smart belt may connect to a first aid component 27, described in more detail below. A data port 58 may also be incorporated in the smart belt 10 to upload, download, sync, and transmit data to and from the microprocessor 12 and data storage devices 20. In at least one embodiment, data port 58 may represent multiple physical data communications systems allowing for a physical data connection between devices and/or device holders coupled to the smart belt 12. Also, in at least one embodiment, data port 58 and charging port 26 may be combined into the same physical device, such as power over Ethernet systems and USB which provide both power and data communications capabilities. For example, some devices and device holders will need only wireless communications capabilities, while others may require only power charging/recharging capabilities, and some others may prefer both a physical charging connection and a physical data connection, such as a detachable video camera that may need to communicate large quantities of data that would be better served by a higher capacity wired connection vs. a wireless connection while also being recharged. The smart belt further includes a component mounting strip disposed on the exterior of the belt that facilitates the mounting of external components to the belt.

The rechargeable power supply 22 in the smart belt 10 may be charged by using inductive charging. An inductive charging system 30 is incorporated within the driver's seat 32 in a vehicle 33, and/or in a specially-equipped chair 34 in a home, office facility or other location to charge the power supply in the smart belt 10. The inductive charging system 30 is incorporated in the seats so that it may inductively couple and charge the power supply 22 in the smart belt 10. The inductive charging system 30 is preferably embedded in the back portion of the vehicular seat or office seat. In this manner, whenever a person wearing a smart belt 10 is sitting in a seat 32 or 34 equipped with the charging system 30, the smart belt power supply 22 receives additional electrical charge to replenish its charge. The user does not need to plug the power supply to an outlet or connect any wires or connectors. Charging occurs when the smart belt 10 comes into proximity with the inductive charging system 30, such as when the wearer is seated in the vehicular or office seat 32 or 34. Contactless inductive energy transfer is known in the art as a convenient way to transfer energy. See for example U.S. Pat. Nos. 6,490,176 and 5,959,433, and published United States Patent Applications, Publication Nos. US 2004/0189,246 and US 2004/0145,343.

The power supply 22 in the smart belt is capable of supplying power to all of the devices coupled to and held by the smart belt via the power strip/data bus 24. The devices are held in sockets or holders that have electrical connections to the power strip/data bus 24 to enable the power and data distribution. The microprocessor 12 is also capable of detecting the power level in any device waning and to distribute power from the batteries of one or more other devices to devices that have low power charge. The microprocessor 12 may also prioritize the devices in the smart belt so that power may be taken from the lower priority devices and distributed to the higher priority devices.

Figure 12:
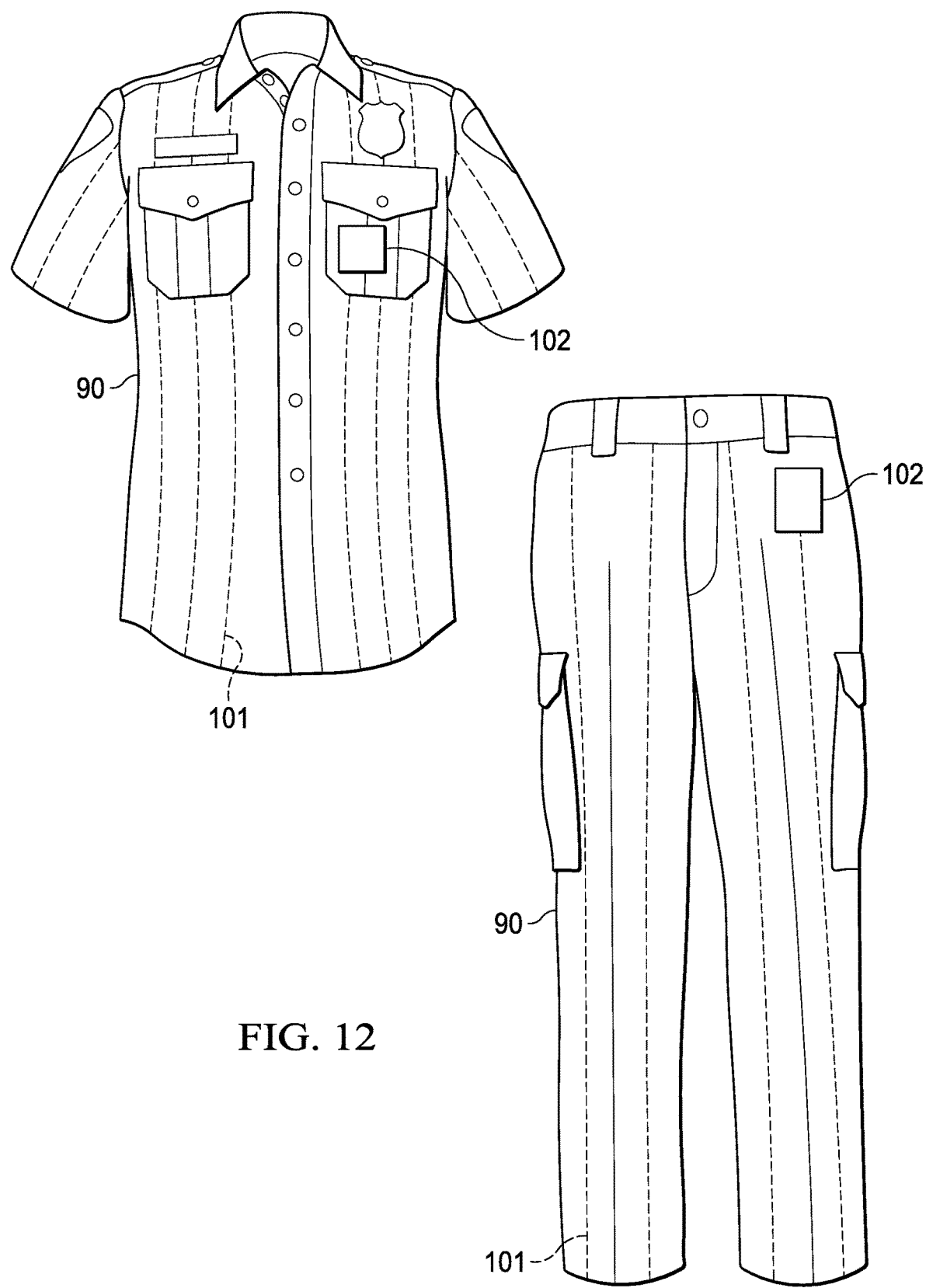
FIG. 12 is an illustration of an embodiment in which conductive wires are incorporated into clothing items to conduct electricity and data signals to the devices and components coupled to special connectors incorporated into the clothing items.

In another embodiment as shown in FIG. 12, the clothing items 90 worn by the user may incorporate conductive wiring or fibers 101 woven into the fabric that may be used to conduct electricity and data signals to devices and components 102 clipped or attached onto connectors disposed at various locations of the clothing items 90. These wires 101 may be coupled to power supply 22 to enable powering the devices and components 102. The wires 101 may also communicatively couple the devices and components 102 to the microprocessor 12 to enable sending and receiving data therefrom. Preferably, the wires 101 are coated to render the outer surface non-conductive. Additionally, the wires 101 are flexible and can be easily and inconspicuously incorporated into the garments 90. In another embodiment, these wiring or fibers 101 are also configured to detect impact, forces, or penetration (by bullet, knife, club, etc.) being exerted on it and generate data in response thereto. The data may correspond to the amount and direction of the exerted force or impact or a message that notifies the microprocessor, so that appropriate action may be taken, such as sending a message to notify a central command post, or perform analysis of the data to determine the origin of the bullet.

Figure 2:
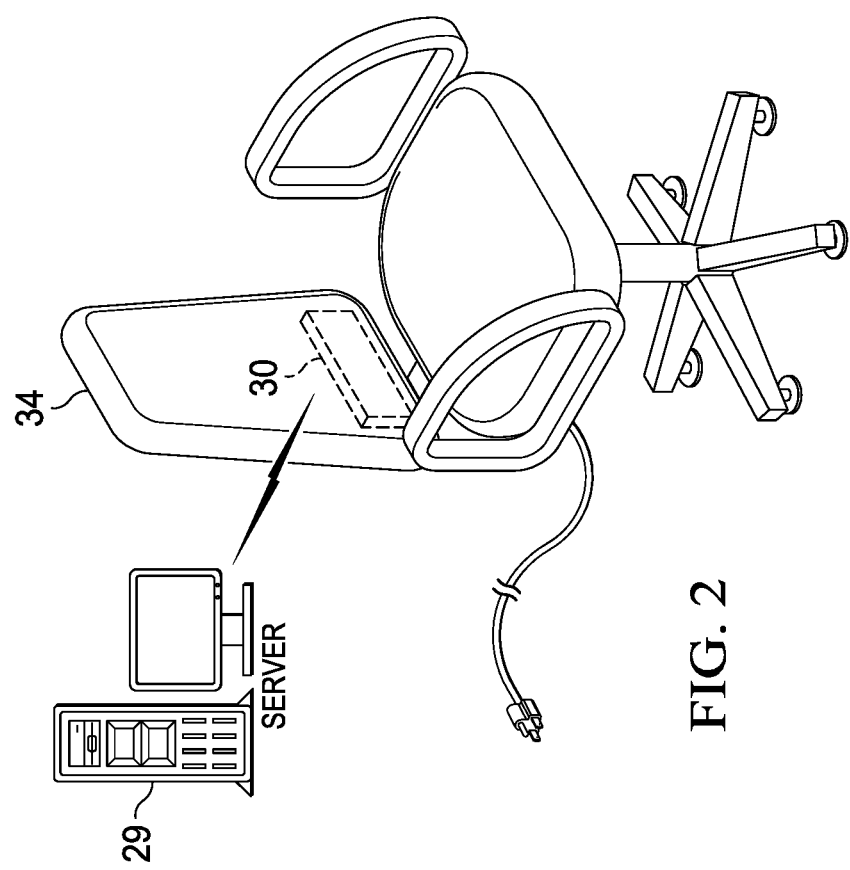
FIGS. 2 and 3 are diagrams illustrating the seat mounted inductive charging configurations according to one embodiment of the present disclosure.
Figure 3:
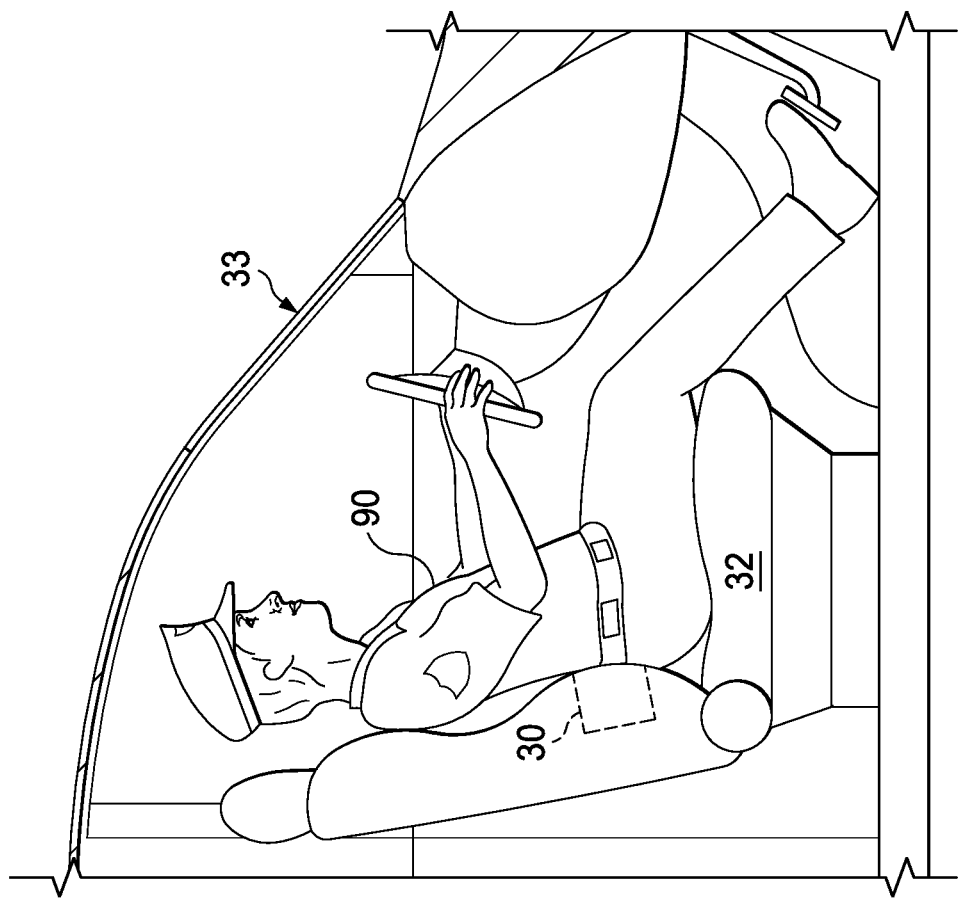
Figure 4:
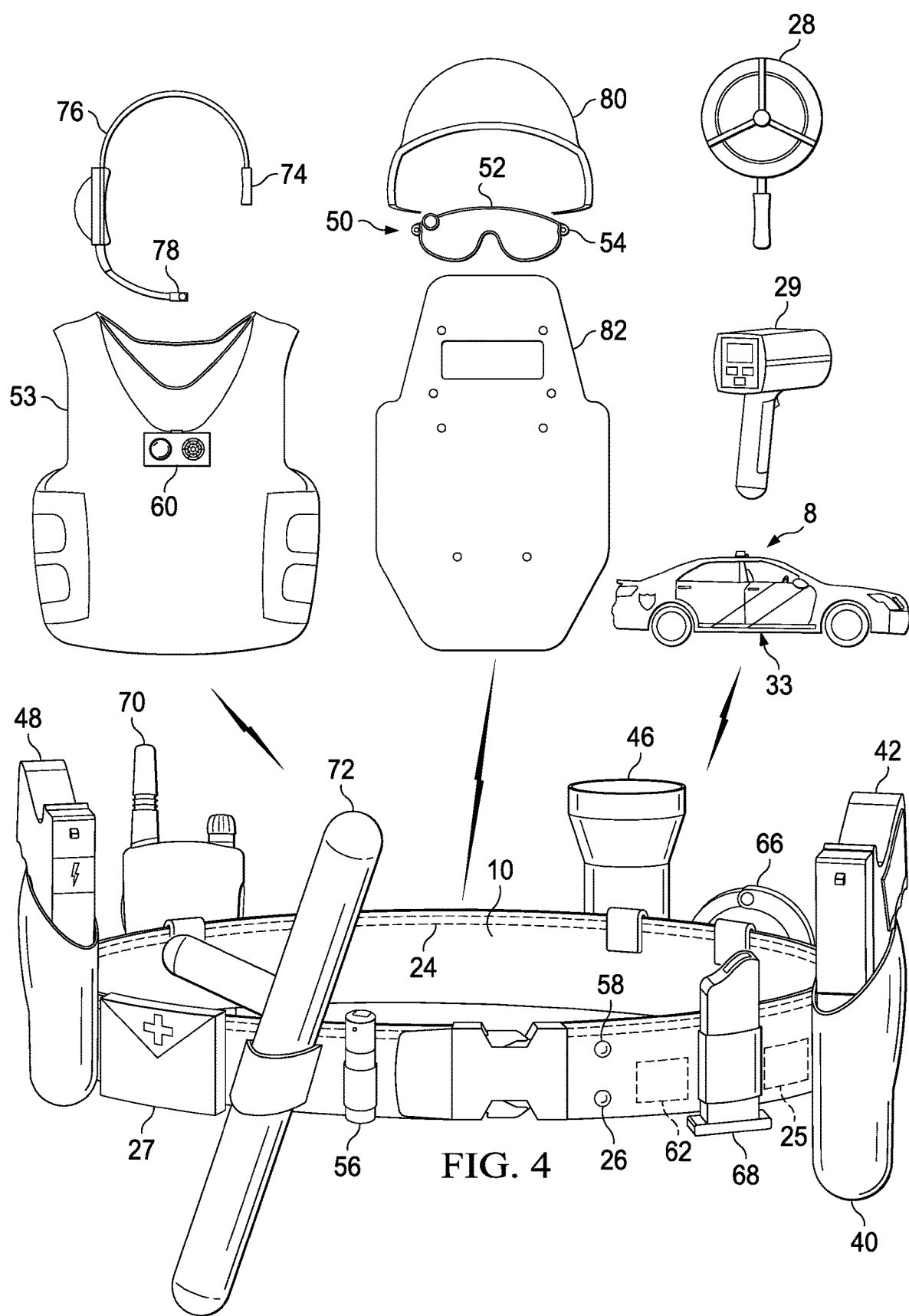
FIG. 4 is an illustration of a myriad of external and internal public safety components wired or wirelessly coupled to the smart belt according to one embodiment of the present disclosure.
Figure 5:
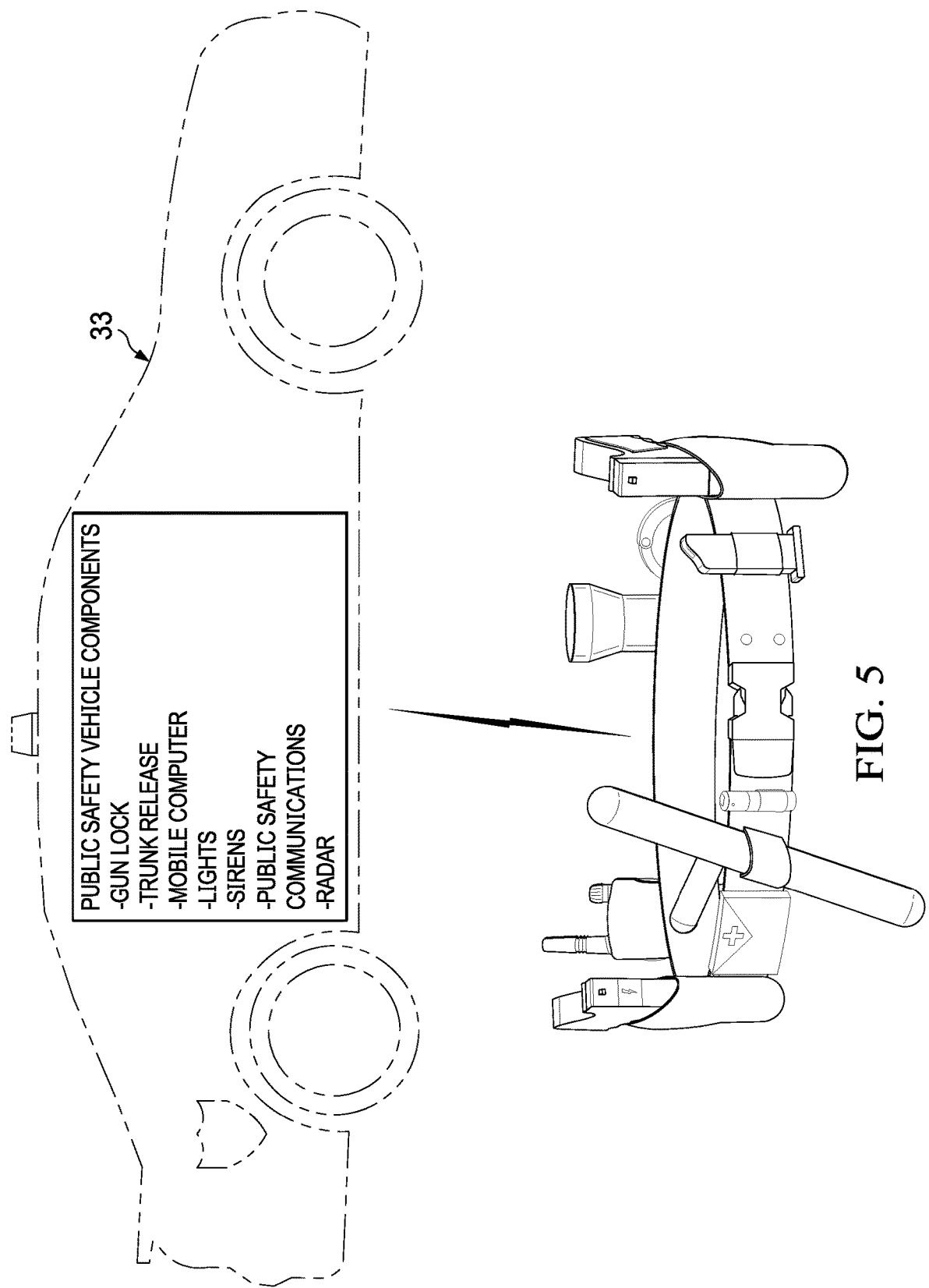
FIG. 5 is an illustration of a public safety vehicle and its components wired or wirelessly connected to the smart belt according to one embodiment of the present disclosure.

In addition, the smart belt 10 may interface with external electronic components wired or wirelessly connected to the smart belt. By way of example, one such component may be a holster 40 (FIG. 2) that is capable of detecting when a weapon 42, such as a gun, is removed from the holster, the number of bullets in the weapon 42, the mechanical status of the weapon, etc. Further, each external component may be equipped with location and orientation detection mechanism such as GPS/accelerometer/gyroscope devices that can detect the position and orientation of the component (e.g., directional, relative to orientation of the smart belt, and with respect to horizontal/vertical). The microprocessor 12 in the smart belt 10 is configured to receive this information and monitor their position/orientation relative to the wearer or some other frame of reference as configured. An analysis of this data may include determining that the position of a component is too distant from the location of the smart belt wearer, and displaying/sounding a warning message along with the location of the component to the wearer, other smart belts, other persons or to a central public safety dispatch or control center. For example, if a police officer has been separated from their sidearm by more than an expected distance, such as a few feet, the police officer and/or a central control center can be notified. The central dispatch or control center also receives the current geo-location of the smart belt to keep track of the position of all of the wearers. The microprocessor in the smart belt may also be configured to enable or disable devices or certain functionalities of a device, based on the position or orientation of the device in comparison to the smart belt or the distance of the device from the smart belt. The holster 40 may also incorporate a mechanism or mechanical lock that would prevent an unauthorized user from removing the weapon 42 from the holster 40 if certain biometric requirements (e.g., fingerprints, handprint, etc.) are not met. The holster 40 may also work in conjunction with the other belt components. For example, when the weapon 42 is removed from the holster 40, it may also cause a video recording system associated with the smart belt 10 to activate and begin recording. In addition, the removal of the weapon 42 may cause the GPS component 16 of the smart belt 10 to send the wearer's location to other wearers or public safety officers in the area or to a central public safety dispatch or control center. The orientation of the weapon 42 is also sensed and relayed to the microprocessor in the smart belt and used in analytics. The microprocessor 12 disposed within the smart belt 10 may control and coordinate the interaction of all connected components on the smart belt 10 to determine the proper action to be taken by any component on the wearer's person or in the vehicle when one or more of the components are activated. The microprocessor 12 may also record the status/activity/GPS coordinates/orientation of the components and store and/or transfer the status/activity data. The microprocessor 12 may also send an alert to other public safety employees or to a central public safety dispatch center or control center, if a certain component or components are activated. The smart belt 10 may convey information/data to the wearer using a number of ways, such as providing a visually-perceivable display on a pair of goggles or eyewear 52, and providing aurally-perceivable information using speakers/earbuds 76, etc. The public safety personnel may receive visual/graphical/audio information related to all of the components associated with the smart belt, including power levels, location/orientation, operating status, central dispatch communications, low fuel level of the vehicle, warning messages, etc.

Examples of what may constitute proper action that can be taken automatically include: logging the location, orientation, and acceleration/movement of the wearer/vehicle/external component(s), begin recording audio/video, begin analysis of audio/video information, begin relaying audio/video information to central dispatch/station, relay wearer's physiological data to central dispatch, sound siren of the vehicle, and turn on an emergency light bar 8 on the vehicle.

The following components, may communicate wired or wirelessly with the smart belt 10:

A radar component 29. The radar component 29 may be a handheld unit, a remote fixed or portable device or a device integrated with the public safety vehicle. When it is activated and being used to measure the speed of passing vehicles, it may relay the measured speed to the microprocessor in the smart belt in a wired or wireless manner, which may project it for viewing by the wearer on the eyewear and/or a display in the vehicle, whichever one that is best suited for the user. If the measured speed exceeds the posted legal speed, the video information captured of the speeding vehicle's license plate and the driver's facial features are automatically analyzed using character recognition and facial recognition software to identify the license plate and the speed violator.

A flashlight component 46. In one embodiment, a flashlight component 46 wired or wirelessly connected to the smart belt 10 may be charged and monitored via the smart belt. If the smart belt 10 detects a problem (i.e., low battery, defective bulb/battery/switch) it may take action to correct the problem or alert the wearer to the problem. If the flashlight device 46 is activated, the smart belt 10 may record the date/time and location/orientation of the device prior to, during and after the activation, further activate any other components of the smart belt 10 as programmed, further send a notification or alert of the activation or status of the device 46.

A taser, stun gun, or an electroshock weapon component 48. In one embodiment, the electronic weapon 48 is wired or wirelessly connected to the smart belt and its power supply may be charged and monitored via the smart belt 10. If the smart belt 10 detects a problem (e.g., low battery, defective probe/battery/switch) it may take action to correct the problem or alert the wearer to the problem. If the electronic weapon device 48 is activated, the smart belt 10 may record the date/time and location/orientation of the device prior to, during and after the activation, further activate any other components of the smart belt as programmed, and further send a notification or alert of the activation or status of the device 48.

A facial recognition system. In one embodiment, facial recognition software installed and executing in the microprocessor 12 may work in conjunction with a video camera 50 and/or 60 wired or wirelessly connected to the smart belt 10. The video camera 50 and/or 60 may be mounted on protective eyewear 52 worn by the user or on an armored vest 53, clothing 90, or smart belt 10 worn by the user, for example. The video camera is operable to scan the faces and postures of people encountered by the wearer of the smart belt 10 and transmit the image data to the smart belt 10 or a remote database or software application for analysis and to take proper action.

A night vision system 54. The night vision system 54 is coupled to the eyewear 52 to enable the wearer of the eyewear 52 to see in environments of low ambient light. In one embodiment, the night vision component 54 is wired or wirelessly connected to the smart belt and may provide 360-degree perimeter movement detection in low light circumstances for the wearer of the smart belt 10, record the activity and the time/date/geographical location of the activity, and transfer the information to the smart belt to take proper action.

A chemical spray component 56. In one embodiment, the chemical spray component 56 is wired or wirelessly connected to the smart belt 10 and may be monitored via the smart belt. If the smart belt 10 detects a problem (e.g., outdated chemicals, low chemical supply, chemical leakage, etc.) it may take action to correct the problem or alert the wearer or a third party of the problem. If the device 56 is activated, the smart belt may record the date/time and location/orientation of the device prior to, during and after the activation, activate any other components of the smart belt as programmed, and further send a notification or alert of the activation or status of the device.

A gunshot detection component 28. In one embodiment, the gunshot detection device 28 may be incorporated into the smart belt and may include one or more microphones or audio sensors that is wired or wirelessly connected to the microprocessor 12 of the smart belt 10 and may sense the sound of a gunshot in the vicinity of the smart belt wearer. Software installed in the microprocessor 22 or elsewhere in the smart belt 10 is capable of analyzing the audio data, detecting gunshots from received audio signals, and determining the probable location of the sniper/shooter. Preferably, multiple microphones are mounted at various locations to enable triangulation analysis to identify the direction and location of the shots, For example, microphones may be disposed on both sides of the user's helmet, armored vest, glasses, face shield, riot shield, and/or smart belt(s). In addition, the smart belt may receive wireless data from remotely mounted gunshot detection listening devices 28, such as mounted on vehicles, street lamps, buildings, etc. The software logic is able to take into account the location of the user (wearing microphones), the location of fixed microphones, and determine the location of the shooter based on the which microphones picked up the audio signature of the shot, Doppler effect in the audio signal, the locations of the microphones, and triangulation analysis. Additionally, data from multiple smart belts may be collected for analysis to pinpoint the shooter location. Once detected, the detection may trigger the activation of other smart belt associated components such as the night vision component 54, video recorder component 60, GPS component 16, and the communication component 14, to automatically send the information to other public safety employees or a public safety facility or other smart belts. It may also use data received via the gunshot detection device 28 or other devices to mathematically or visually determine the possible location of the origin of the gunshot and map the location to be graphically displayed to the wearer of the smart belt visually via glasses or face shield with video and graphical capabilities that are wired or wirelessly associated with the smart belt.

In an alternate embodiment or in augmentation to audio signal analysis, items worn and/or held by the user (e.g., helmet, riot shield, armored vest, uniform) may include embedded sensor networks that can take a bullet strike, and wirelessly relay sensor data associated with the bullet strike to a microprocessor (such as the one on the smart belt). The microprocessor may analyze the sensor data (e.g., force, pressure, velocity, direction, location on the item, location of the item, and which direction the surface struck by the bullet faces) to determine the caliber of the bullet and the incident angle and velocity of the bullet strike, and further determine the direction from which the bullet traveled and ultimately the location of the shooter. Data sent to the microprocessor for analysis may also be provided by other remote data sources such as The National Weather Service, The National Oceanic and Atmospheric Administration, etc. and may include data including, but not limited to weather, wind direction, mapping or aerial photography An environmental sensor component 62. In one embodiment, the environmental sensor component 62 is wired or wirelessly connected to the microprocessor 12 of the smart belt 10 and may detect chemical or biological hazards in the environment of the smart belt wearer, take action by activating additional components of the smart belt, and notifying the wearer of the smart belt 10 and others.

An audio recording component. In one embodiment, the audio recording component is part of the video recording component 60 described above, but they may be separate independent subsystems. The audio recording component 60 is wired or wirelessly connected to the smart belt 10 and may be voice activated and integrate with the Global Positioning system component 16 and be either manually activated to begin recording or begin recording based on certain criteria, e.g., the detection of sound at a certain geographical location. For example, if a police officer is at the police station the device will not record, however if the officer in proximity to residence known for illegal drug activity it may begin to automatically record. In another embodiment, the audio recording device may integrate with voice recognition software to allow the public safety employee to control the function of the smart belt and the wired or wirelessly connected external or internal components via voice commands. In another embodiment, the audio recording component may integrate with a voice recognition component operable to compare the audio pattern and characteristics of voices detected to a digital library of known voices to identify the person detected. Further, the audio recording component may be integrated the video eye glasses 52 that are wired or wirelessly connected to the smart belt 10 to display the picture and information to the smart belt wearer based on the identification of the individual by the audio recording component.

A video recording component 60. In one embodiment, the video recording component is wired or wirelessly connected to the smart belt and may be voice activated and integrate with the Global Positioning component 16 and be either manually activated to begin recording or begin based on the detection of sound at a certain geographical location. For example, if a police officer is at the police station the device will not record, however if the officer in proximity to residence known for illegal drug activity it may begin to automatically record received video signals. In another embodiment, the video recording component 60 may integrate with the facial recognition component. For another example, the video recording component 60 may automatically begin recording if the smart belt 10 is within a predetermined distance, such as 40 feet, from another human being, such as a person encountering a police officer. Continuing this example, the video recording component 60 could also not be activated if the only other human being(s) in the area is also wearing a smart belt, such as another police officer to avoid recording when only police personnel are present. If the facial recognition component identifies a person or persons in the officer's vicinity with an arrest/conviction record and/or a history of aggression on police officers, it may begin recording. In another example, if firefighting personnel wearing smart belts are at the scene of a fire and the facial recognition component identifies a known arsonist in the area around the fire personnel wearing smart belts, the recording component may activate and also send the information from the video recording component and the global positioning component or via an electronic alert or other message to a central command and/or public safety employees or other personnel in the area who are also wearing their smart belts.

A handcuff component 66. In one embodiment, the handcuff component 66 is wired or wirelessly connected to the smart belt 10 and when the handcuff 66 is removed from its case in the belt, the GPS component 16 is activated to automatically record the location and also to activate the audio component and/or video component to document the surrounding activity, including the arrest. In addition, sensors or devices may be disposed within handcuff component 66 to measure and/or monitor the vital signs of the wearer including, not limited to, blood pressure, pulse rate, body temperature or respiration. The vital sign information may be constantly or periodically gathered by the sensors or devices disposed within handcuff component 66 and transmitted to a central monitoring location, a remote computerized monitoring system or a person, either via the wired or wirelessly connected smart belt 10 or a direct connection to an external communication network utilizing a communications component communicatively coupled to handcuff component 66.

A first aid component 27. In one embodiment, one or more items such as a tourniquet may be part of a first aid component 27 that are wired or wirelessly connected to the smart belt 10. The removal of the tourniquet and/or another from the first aid component would automatically cause the activation of the communication component to send a live or pre-recorded message to the public safety dispatch center or other public safety employees or other personnel in the vicinity. It may also automatically trigger the location stamping of the location by the GPS component 16, the location being sent with the message by the communication component to a central dispatch or communications center or to other public safety employees or other personnel or other smart belt wearers in the vicinity. In addition, sensors or devices may be disposed within first aid component 27 to measure and/or monitor the vital signs of the patient including, not limited to, blood pressure, pulse rate, body temperature or respiration. The vital sign information may be constantly or periodically gathered by the sensors or devices disposed within first aid component 27 and transmitted to a central monitoring location, a remote computerized monitoring system or a person, either via the wired or wirelessly connected smart belt 10 or a direct connection to an external communication network utilizing a communications component communicatively coupled to first aid component 27.

An ammunition storage component 68. In one embodiment, the ammunition storage component 68 is wired or wirelessly connected to the smart belt 10 and may monitor the age or condition of the ammunition contained in the ammunition storage component 68 and notify the wearer of the smart belt (via the microprocessor 12) if a problem is detected with the ammunition. In addition, the component may recognize incompatible ammunition as compared to the weapon 42 detected in the firearm holster component 40 and compare the information and notify the wearer of the smart belt 10. In addition, when ammunition is removed from the ammunition storage component 68 it may cause other components wired or wirelessly connected to the smart belt 10 to activate and operate.

A communication device component 70. In one embodiment, the communication device 70 is wired or wirelessly connected to the smart belt 10 and allows two-way audible communications between the smart belt wearer and other smart belt wearers or a public safety dispatch center. The communication device component may also function to transfer data to and from the smart belt or the external or internal components wired or wirelessly connected to the smart belt, to and from external computer systems, voice or data analytics systems or voice or data storage systems. The communication device component may also work in conjunction with a software component disposed within the smart belt or the smart belt components, to identify components in need of software updates and transmit the data related to the update to the component.

A baton component 72. In one embodiment the baton device 72 is wired or wirelessly connected to the smart belt 10 and works in conjunction with software disposed in the baton component 72 or the smart belt 10, the software component working in conjunction with the microprocessor 12 in the smart belt 10 to recognize the removal of the police baton 72 from the smart belt and cause the GPS component 16 to create a digital stamp of the location/orientation of the device prior to, during or after deployment, the communications device component 70 to send a notification to other smart belt users in the area or a police dispatch facility indicating that the baton 72 has been removed from its holster. The baton's removal may also cause the audible recoding component, the video recording component, and the facial recognition component to be activated and begin recording. The baton device 72 may also have a biometric component that detects usage by unauthorized person and activates other components of the smart belt and takes action to notify other public safety employees, other smart belts and/or a public safety dispatch center.

A holster component 40. In one embodiment, the holster 40 is wired or wirelessly connected to the smart belt 10, with the weapon 42 contained within the smart belt wired or wirelessly connected to either the holster or the smart belt. The holster may monitor the condition and status of the weapon contained within the holster including, but not limited to the number of bullets in the weapon, if there is a bullet in the chamber of the weapon, the status of the weapon, the number of rounds fired by the weapon and the caliber of the weapon. The holster or smart belt may further detect the removal of the weapon 42 from the holster 40 and the removal of the weapon from the holster may further cause the holster or the smart belt to further activate the audio recording component, the global positioning component, the video recording component, the communications component, the night vision component, and/or the eyewear component or any other component of the smart belt The weapon 42 component. In one embodiment, weapon 42 is a firearm wired or wirelessly connected to the smart belt 10, the smart belt 10 operable to monitor the status of the firearms component including the readiness of the firearm to fire, the usage history of the firearm including the number of times it has been removed from the holster and fired and the location/orientation of the firearm prior to, during or after the firearm is fired. The weapon 42 may also contain a biometric component that prohibits unauthorized users from using the weapon by reporting the biometric information to the smart belt, the smart belt operable to determine that the user is not authorized and disabling the weapon, and further activating other components of the smart belt including but not limited to the GPS component 16, the video recording component, the communications component and the audio recording component. The smart belt 10 may also notify other smart belt users, other public safety employees or a public safety dispatch center of the status of or use or attempted use of the weapon. The firearm may use traditional primer, casing, powder, and projectile type ammunition or alternate unique ammunition to discharge various objects, projectiles, or substances. In addition, sensors or devices may be disposed within weapon component 42 to measure and/or monitor the vital signs of the user including, not limited to, blood pressure, pulse rate, body temperature or respiration. The vital sign information may be constantly or periodically gathered by the sensors or devices disposed within weapon component 42 and transmitted to a central monitoring location, a remote computerized monitoring system or a person, either via the wired or wirelessly connected smart belt 10 or a direct connection to an external communication network utilizing a communications component communicatively coupled to weapon 42.

In addition, the wireless communications component 14 disposed within the smart belt may act to receive software updates for the smart belt itself, as well as the components connected wired or wirelessly to the smart belt.

In addition, the smart belt may be wired or wirelessly communicatively coupled to external devices removed, removable or separate from the smart belt including:

Eyewear 52 wired or wirelessly communicatively coupled to the smart belt 10 equipped with an internal projection system to provide data, images or video to the wearer received from the wearer's smart belt or its related components or received from other smart belts worn by other public safety employees.

A headset 76 incorporating an ear piece 74 and microphone 78 wired or wirelessly communicatively coupled to the smart belt 10 to provide two-way audio communication via the smart belt or its related components or received from other smart belts worn by other public safety employees.

Ballistic headwear 80. The ballistic headwear 80 or helmet wired or wirelessly communicatively coupled to the smart belt 10 being operable detect impact and measure the degree of impact to the ballistic headwear, or change in orientation of the ballistic headwear, and transfer the information to the smart belt 10 for analysis and take action.

A ballistic vest 53. The ballistic vest wired or wirelessly communicatively coupled to the smart belt 10 is able to detect impact to the ballistic vest and measure the degree of impact, or change in orientation of the ballistic vest, and transfer the information to the smart belt for analysis and take action. In addition, sensors or devices may be disposed within ballistic vest 53 to measure and/or monitor the vital signs of the wearer including, not limited to, blood pressure, pulse rate, body temperature or respiration. The vital sign information may be constantly or periodically gathered by the sensors or devices disposed within ballistic vest 53 and transmitted to a central monitoring location, a remote computerized monitoring system or a person, either via the wired or wirelessly connected smart belt 10 or a direct connection to an external communication network utilizing a communications component communicatively coupled to ballistic vest 53.

A ballistic shield 82. The ballistic shield 82 wired or wirelessly communicatively coupled to the smart belt 10 is capable of detecting impact or change in orientation of the ballistic shield and transfer the information to the smart belt to take action.

In addition, the public safety vehicle 33 itself may wired or wirelessly connect as a component of the smart belt 10. The public safety vehicle 33 may be equipped with sensors to detect glass breakage, intrusion, force applied to the exterior or malfunctions and transfer the information to the smart belt to take action. The sensor may detect glass breakage (sniper fire/car accident/attack while the vehicle is occupied or unoccupied) and send a warning message to the belt wearer (if away from the car) or a centralized monitoring station.

In addition, the ballistic shield 82, helmet 80, vest 53, clothing 90 (e.g., shirt, trousers, hat, shoes), and public safety vehicle may be further equipped with external or internal sensors to detect a number of variables. For example, temperature sensors may be used to determine the body temperature of the officer to detect overheating or other less than optimal environment. The officer's physiological condition may also be measured by a plurality of sensors and relayed to the smart belt. Sensors can also be incorporated to detect the presence of environmental hazards. Sensors may be incorporated into the clothing to determine whether a force exceeding a certain magnitude has been applied to any of the components, determine a velocity and direction vector of the force, and transmit the location information (received from GPS component) to the smart belt 10. The smart belt 10 is operable to analyze the received information and determine the possible location of the origin of the force/hazard, and take action by alerting the wearer or other public safety personnel in the area or a central public safety dispatch center or control center of the possible location of a suspect or threat based on the analysis. In addition, sensors or devices may be disposed within helmet 80 or clothing 90 to measure and/or monitor the vital signs of the wearer including, not limited to, blood pressure, pulse rate, body temperature or respiration. The vital sign information may be constantly or periodically gathered by the sensors or devices disposed within helmet 80 or clothing 90 and transmitted to a central monitoring location, a remote computerized monitoring system or a person, either via the wired or wirelessly connected smart belt 10 or a direct connection to an external communication network utilizing a communications component communicatively coupled to helmet 80 or clothing 90.

In addition, the smart belt 10 may act as an electronic "key" to authorize the operation of the functions of the public safety vehicle 33. In one embodiment, the smart belt is wirelessly connected to the public safety vehicle and when the smart belt is in proximity to the public safety vehicle it provides a digital authorization for the vehicle to be started. In another embodiment, the smart belt provides a digital authorization for a weapon to be removed from a locking gun lock located within the vehicle. In another embodiment, the mobile data computer mounted in the public safety vehicle will accept a digital verification from the smart belt and allow access to the computers operating system by the authorized wearer of the smart belt.

Figure 6:
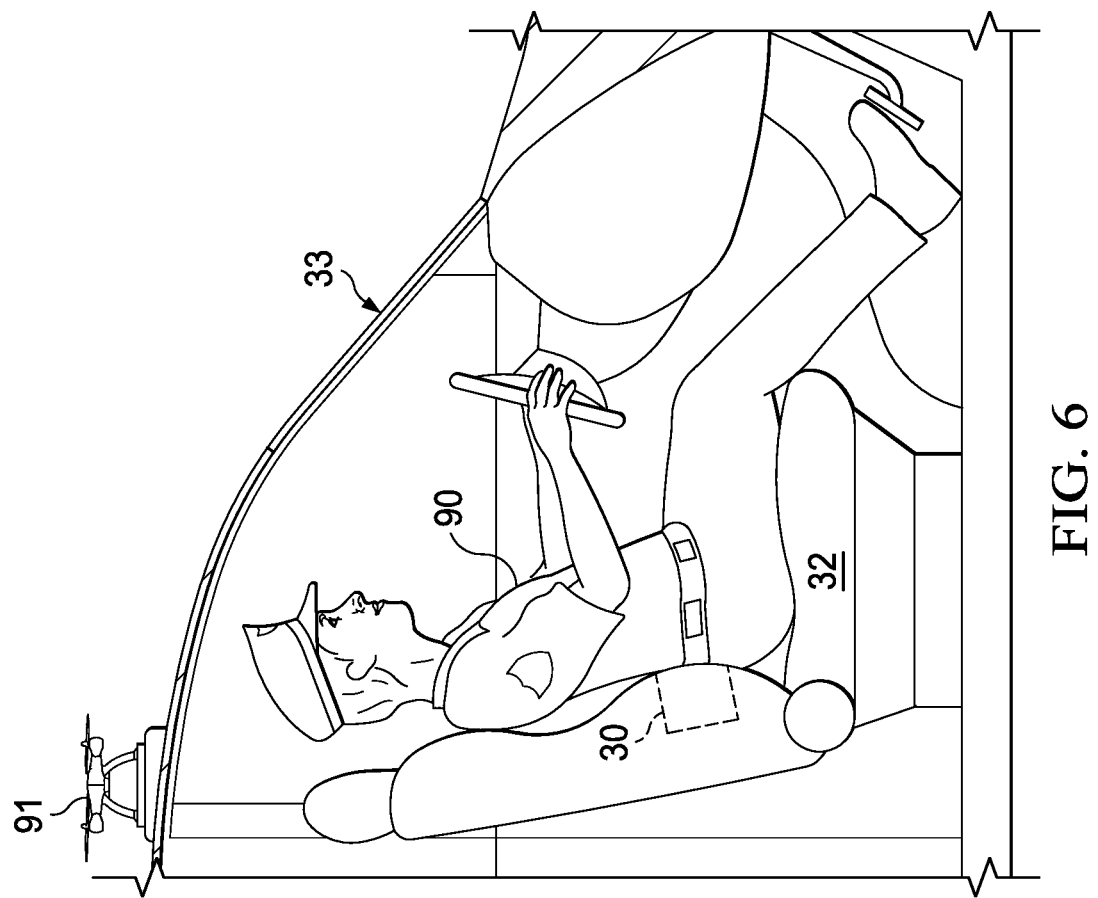
FIG. 6 is an illustration of drone technology incorporated with a public safety vehicle equipped with seat mounted inductive charging for a smart belt according to one embodiment of the present disclosure.
Figure 7:
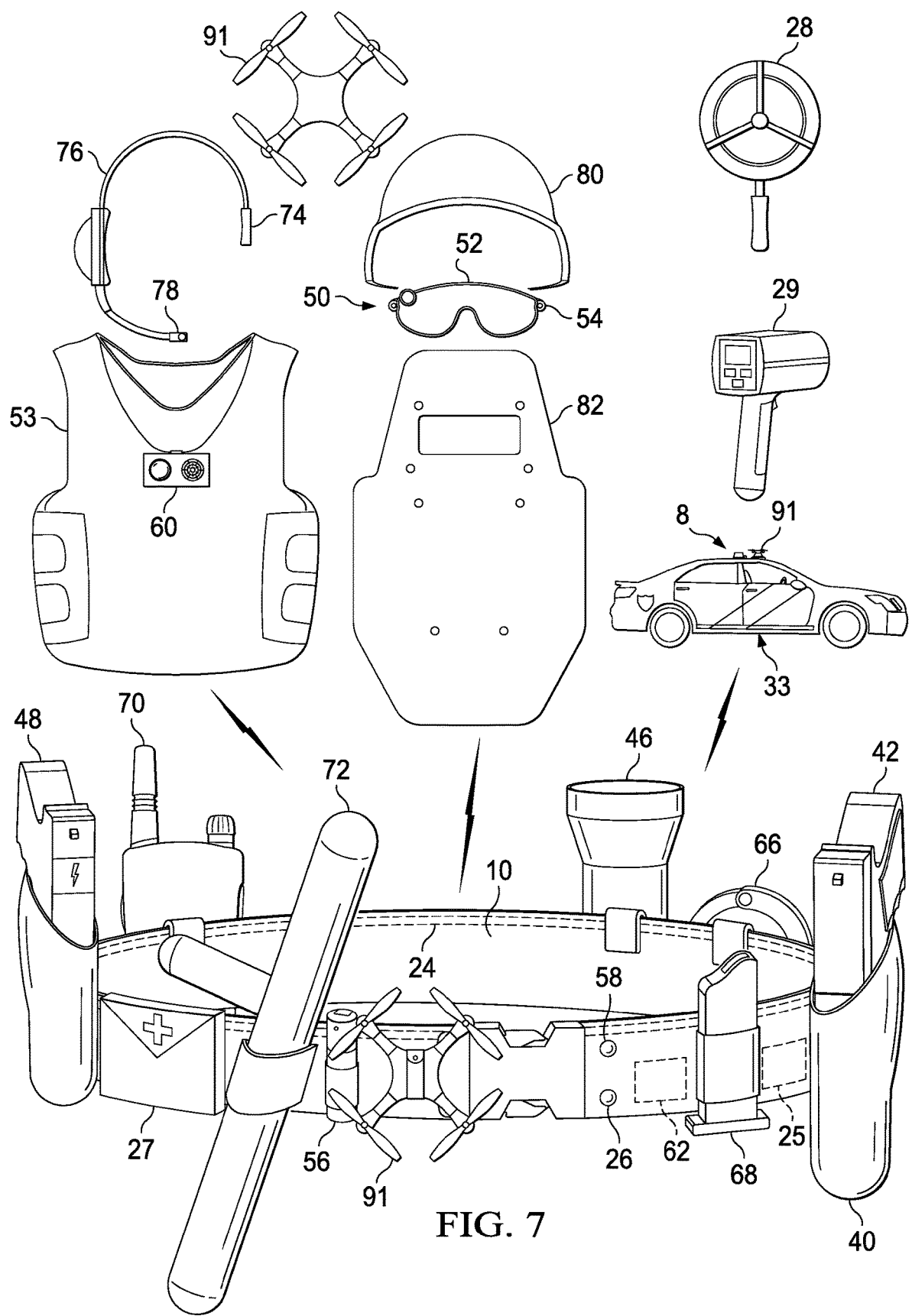
FIG. 7 is an illustration of a myriad of external and internal public safety components including drone technology wired or wirelessly coupled to the smart belt according to one embodiment of the present disclosure.
Figure 8:
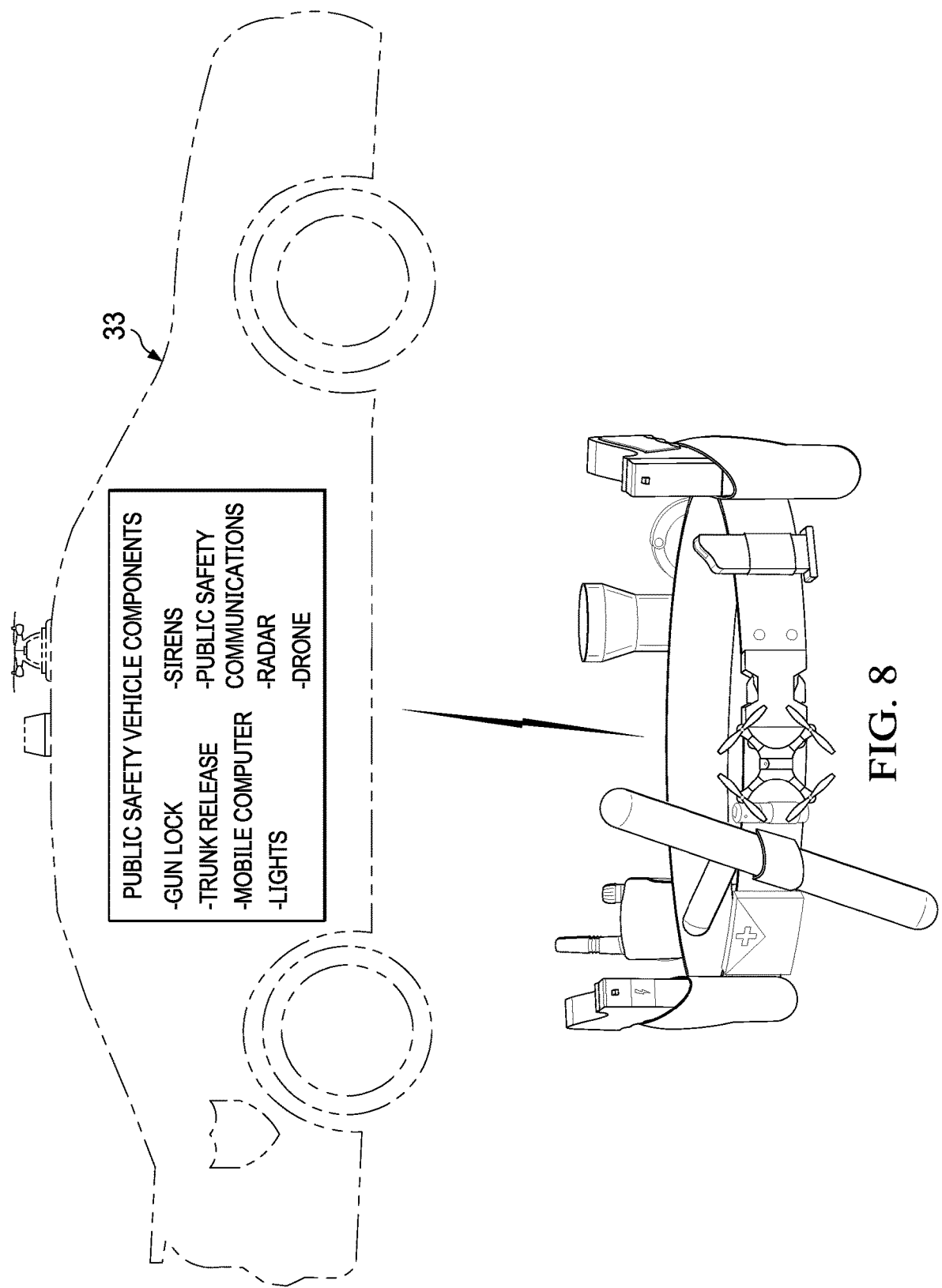
FIG. 8 is an illustration of a public safety vehicle and its components wired or wirelessly connected to the smart belt according to one embodiment of the present disclosure.
Figure 9:
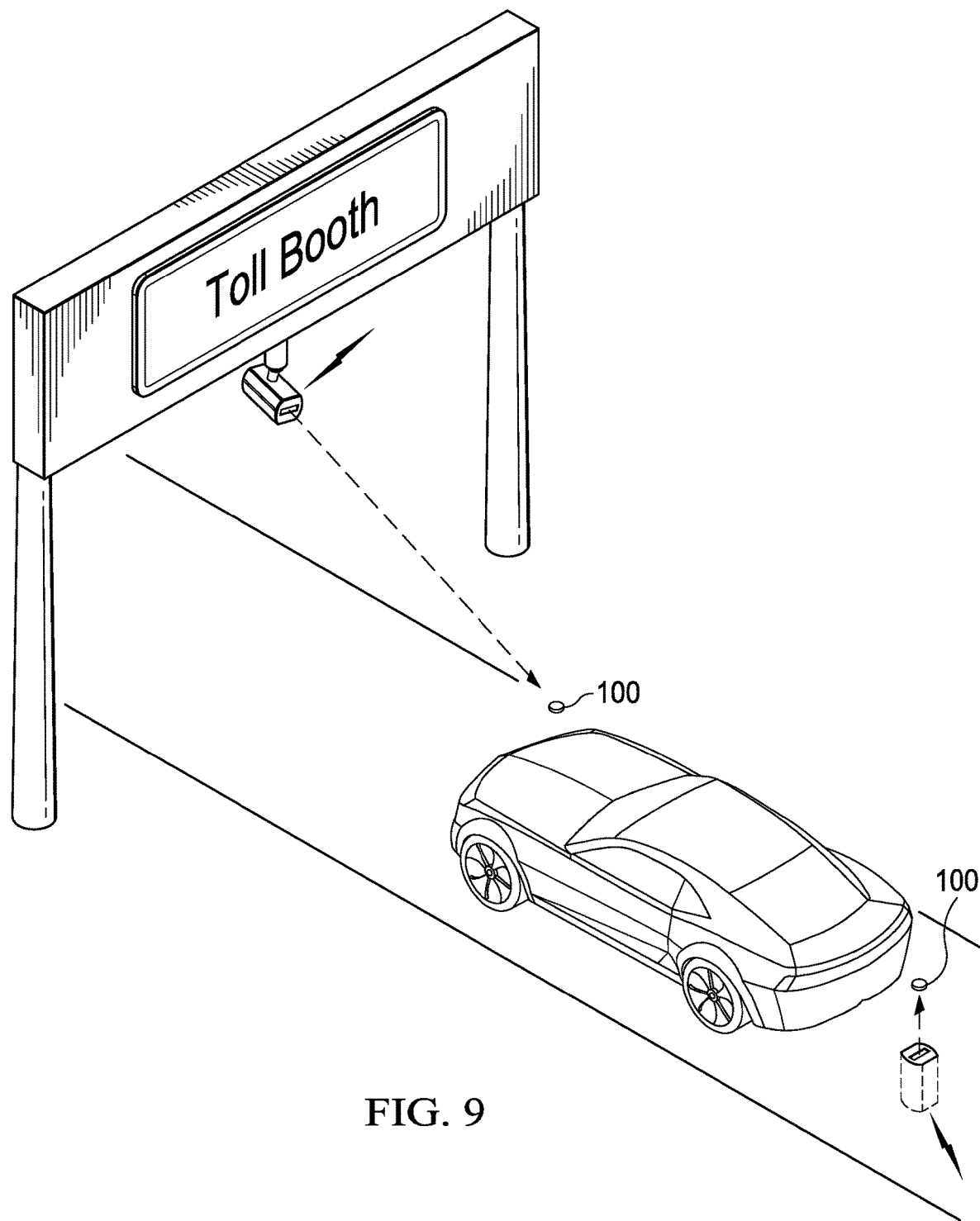
FIGS. 9-11 illustrates various scenarios in which a tracking device may be affixed to a vehicle according to embodiments of the present disclosure.
Figure 10:
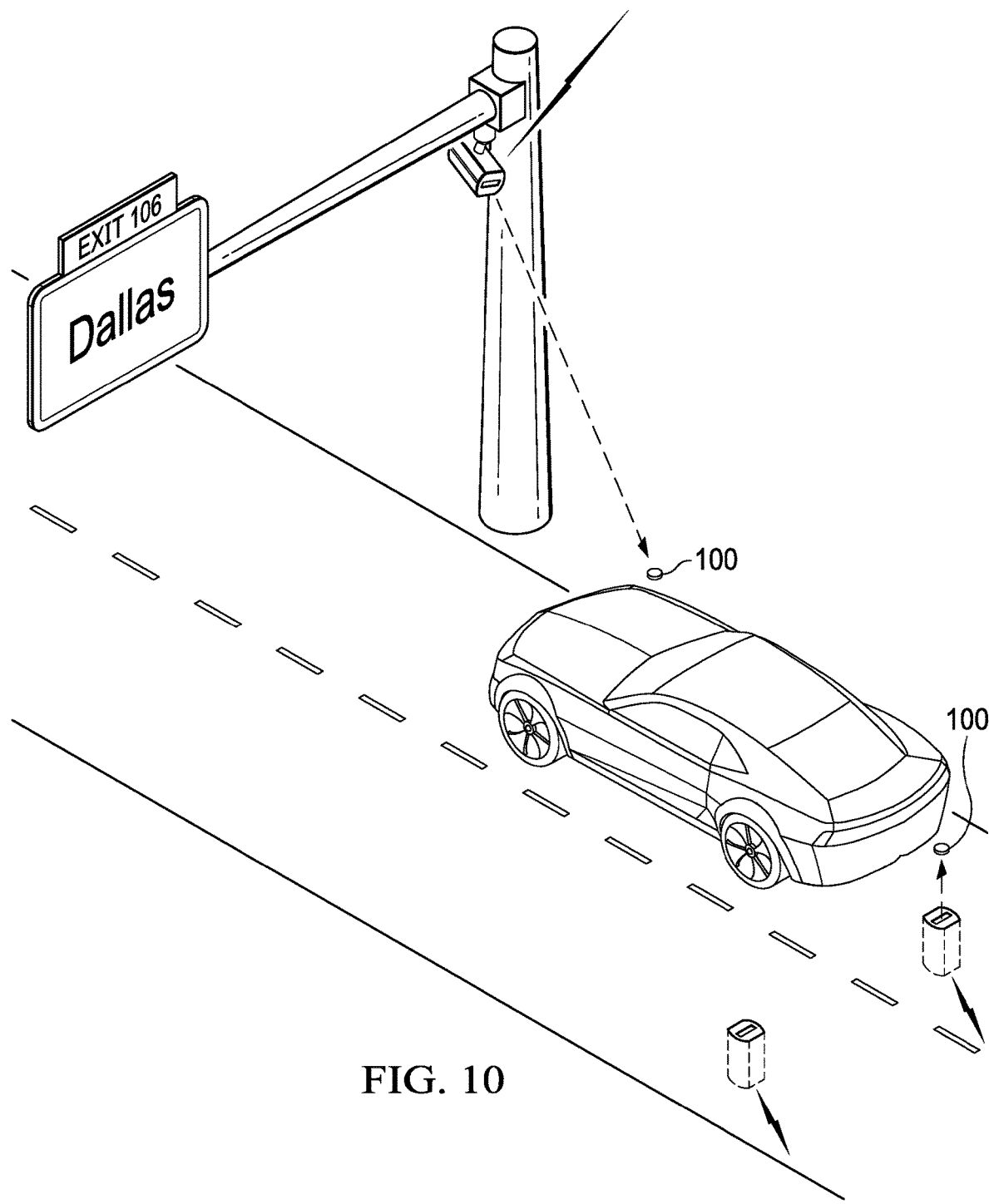
Figure 11:
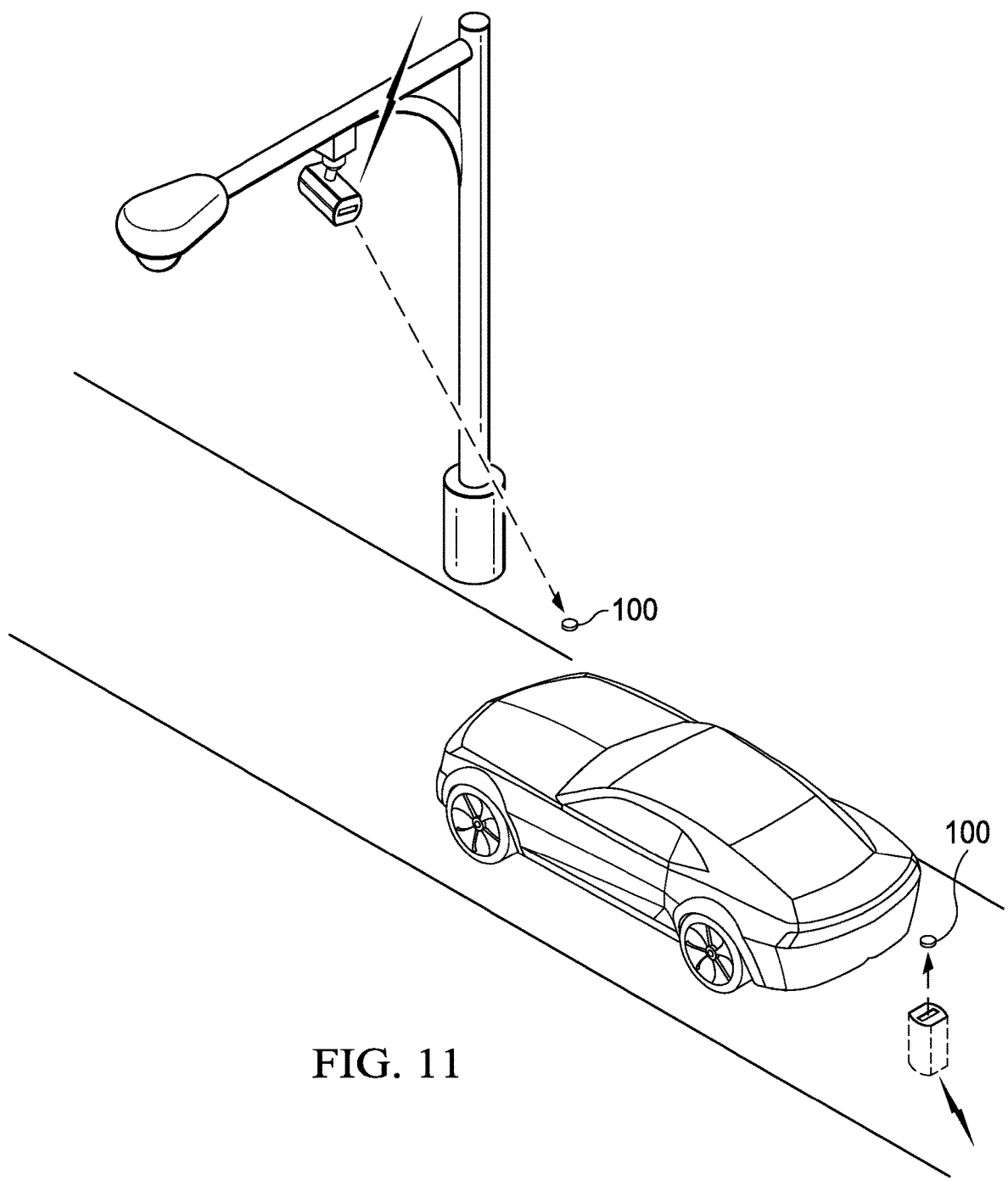

FIGS. 6-8 provide further illustrations of drone technology 91 incorporated as a component of the smart belt 10 for a public safety officer. Three types of drone technology 91 are contemplated herein in various embodiments, which may be combined: (1) a drone that is mounted to the public safety vehicle, (2) a drone that is mounted or holstered on the smart belt 10 or otherwise carried by a human, and (3) a drone that can be launched separately from the public safety vehicle and officer. The vehicle-mounted drone can be located in the interior or on the exterior of the vehicle. When an officer is in chase with a suspect vehicle, he/she can launch a drone after the suspect vehicle is tagged with a tracking device 100. The tracking device 100 can be planted by (1) placing a strip containing one or more tracking devices 100 in the path of the suspect vehicle, which allows one or more tracking devices 100 to be embedded in its tire(s) or otherwise attached to the suspect vehicle such as a strip of magnetic and/or electro-magnetic devices and/or a micro marker, nano device, or GPS device that would be attracted to and attachable to the metallic undercarriage (or other portions) of a vehicle; (2) placing a planting device in the path of the suspect vehicle that shoots or otherwise propels a tracker device 100 at the undercarriage of the suspect vehicle as it approaches or drives over the planting device, (3) shooting a tracking device 100 onto the suspect vehicle by a special weapon used by other officers as the suspect vehicle passes by, and (4) dropping or propelling a tracking device 100 at a vehicle from above, such as a tracking device dispenser mounted at an automated or manned tollbooth, a traffic control device (such as a traffic light), an aircraft, drone, or an overhead directional sign (such as a freeway directional sign), as shown in FIGS. 9-11. The smart belt may include a holster to hold the tracking device special weapon. Similarly, an alternate type weapon 42 may be used to launch or propel a tracking device such as a micro marker, nano device, or GPS device onto a suspect running on foot from the officers in order to tag that suspect and allow tracking of that suspect. In both scenarios the drone may be launched and pursue the suspect who is on foot or in a vehicle using either visual tracking by a user in control of the drone or data supplied to the drone by the attached device or marker, while transmitting GPS location data and live video feed to the pursuing officers (also on foot or in a vehicle) via the video display glasses 52 worn by the officers. The microprocessor 12 in the smart belt 10 remains in wireless communication with drone to send launch, navigation, and operational commands, receive video data, status data, and location data, and transmit other data bi-directionally.

In various embodiments drone technology 91 may comprise submersible, wheeled and/or flyable/airborne type drone units. For example, a lifeguard may have a waterproof version of smart belt 10 with underwater suitable goggles where the lifeguard deploys a small submersible drone. The small submersible drone then searches for movement under the waves in the area of a drowning victim to pinpoints or narrow down the location of a drowning victim. The submersible drone then sends various information to the underwater googles, such as direction commands to a graphical display of the watertight goggles (for example, a simple directional marker to turn left or right or a more complex display such as a dot on a map), GPS coordinates of the possible or general location of the drowning victim, and/or video and/or audio data. The drone could also sound an audible noise or disperse a dye, balloons or other marker in the water to mark the location.

For another example, a police officer at the scene of a hostage situation or a potentially burglarized building may deploy a drone to either fly or move via wheels throughout the location while drone is in wireless communication with the glasses via the smart belt, such as to communicate video and/or audio information from the drone to the police officer. Similarly, fire department personnel may use the drone to check for trapped people in a building that is on fire or to determine whether a fire fighter can enter an area. For example, a drone deployed in a burning building can look for heat signatures consistent with humans or pets, or sounds of distress and cries for help or heat sources to allow fire personnel to be more effective and safe while battling the fires.

In various embodiments, drone technology 91 may be a wheeled, flyable and/or submersible drone equipped with one or more of (a) a dispenser to deploy flares, beanbag rounds, pepper spray and/or other lethal or less-than-lethal items; (b) a delivery capability to provide first aid equipment, ammunition, communication devices, etc.; (c) a camera to allow inspection of a vehicle or location, such as a pipeline or utility system, from a safe distance, to support facial recognition (as described elsewhere); (d) a chemical detection capability to detect chemicals, drugs, particulates, odors, smoke, etc. to allow generation of related information and alerts, such as based on an analysis performed by microprocessor 12 or drone technology 91 itself; and/or (e) a bomb detection capability to allow generation of related information and alerts. In addition, drone technology 91 could be equipped with a motion sensor. The motion sensor equipped drone could then be placed at a location where entry is prohibited or monitored, such as outside a prison yard or entry to a secured location. When the motion detector equipped drone detects a person or movement in the monitored or prohibited area (for example, a person running from a building, going into a building, going over a fence or running from a detention facility) the drone self-launches, alerts a user of the smart belt or another person, and begins pursuit of the detected person while sending data back to the goggles via the smart belt. For example, such a motioned detector equipped drone could protect a public safety vehicle while a police officer is away or allow an officer to monitor multiple locations places at once, such as the front and the back entrance of a suspect's residence.

In one embodiment, the tracking device is an active tracking device that emits an electromagnetic signal that is receivable by a drone or other receiver device. For example, the tracking device could emit a radio beacon that allows a drone or other receiver to determine the direction and/or distance of the signal. This type of tracking device could be relatively inexpensive and have a longer duration due to the simplicity of the transmitter and electronics. An appropriately configured drone may be able to automatically track this type of radio beacon tracking device. In another embodiment, the tracking device is an active tracking device that transmits a GPS signal to a receiver, such as the drone, a satellite, a specialized receiver or a cellular phone tower receiver, that indicates the position of the tracking device. This type of tracking device would allow the receiver to track the location of the device independently of the location of the receiver and the tracking device. In yet another embodiment, the tracking device could be passive, such as a light emitter or a substance, such as paint or dye, which is highly visible under certain conditions. For example, a passive light emitter could emit non-visible or visible light that is trackable via a camera on a drone, the human eye and/or a camera, such as a traffic camera, sensitive that particular color of light. For another example, a high visibility paint could be used, or a paint that reflects strongly in the non-visible spectrum, such as the infra-red spectrum or ultraviolet spectrum, which would allow a pursuing officer, helicopter or drone to manually or automatically track the tracking device and thus the suspect. One or more of the tracking devices could be combined. For example, in a high-density such as New York City, GPS devices may be unreliable due to the inability of the tracking device to locate satellites while between tall buildings, and the tracking device could have the GPS transmitter supplemented with the radio beacon transmitter to allow a drone hovering above the buildings to track the beacon even while the GPS signal was inaccurate. Continuing this example, the tracker could also emit a strong infra-red light, which would allow a drone or a human controlled helicopter (or even a human sitting in a control center watching traffic cameras that are sensitive to infra-red light) to detect and follow the light source if a building is blocking both the GPS signal and the radio beacon signal.

In various embodiments, drone technology 91 uses a drone that may be autonomous, semi-autonomous, under manual control or has some combination thereof. In general, an autonomous drone would be able to automatically determine paths and avoid obstacles that would prevent the drone from reaching or finding the tracking device. In general, a semi-autonomous drone may have some ability to determine paths, avoid obstacles and/or find the tracking device, but requires assistance from a human operator in one or more situations. In general, a drone under manual control requires a human to perform all or virtually all of the drone's navigation. A particular drone may be autonomous for certain functions, semi-autonomous for certain other functions and require manual control in yet other functions. For example, a drone attachable to the smart belt may be launched by the human carrying it, fly up to a certain height, and then require manual control from a different human or a remote computer in order to navigate to the tracking device. For another example, a large drone that can be launched from a vehicle may automatically begin tracking the tracking device and communicating other information, such as speed and a video feed.

In various embodiments, drone technology 91 may include one or more of a video generation system, such as a camera, a system for moving the video generation system, and the ability to communicate video data via a wireless communication system to a remote location. Drone technology 91 may also be attachable to the smart belt 10 or can be carried by a human, such as a drone in a backpack. In this embodiment, drone technology 91 may be chargeable via the smart belt 10, or other carrying device such as a backpack.

In various embodiments, drone technology 91 may be used to track a suspect, such as a suspect fleeing from a pursuing public safety official, such as a police officer. Drone technology 91 may also be used for search and rescue, reconnaissance, surveillance and other activities.

The microprocessor is configured to analyze the captured video images to determine a license plate identifier and/or suspect identification (using facial recognition), and determine one or more addresses associated with the license plate and/or suspect. A "smart mapping" system may be part of or in communication with the smart belt 10 to compare the license plate information of the suspect vehicle or the name of the suspect to determine known addresses for the suspect and/or information, such as addresses, associated with known associates of the suspect. These can be addresses of residence, family members' homes, close associates homes, etc. that the suspect may target. These known addresses can be used to plot out anticipated paths from the current location of the suspect to create a "forecast" so that wearers may attempt to intercept the suspect. In addition, the "smart mapping" component may compare the location of the fleeing suspect or vehicle to a database of known offenders or persons of interest known to reside in or frequent the area and present a listing of possible identities and related information to the wearer. The "smart mapping" database may be contained on the drone itself, on the smart belt, on a computing device housed within a vehicle wired or wirelessly connected to the smart belt or drone, or maintained at a remote location and wirelessly connected to one or more of the drone, the smart belt or the computing device housed within a vehicle wired or wirelessly connected to the smart belt or drone. Also, in the absence of knowledge of the identity of the tracked individual, such as a suspect, the addresses for known criminals in the area may be presented. Further, these known criminals may be further filtered by known characteristics of the tracked individual to provide a higher probability of presenting information relevant to the tracked individual, such as race, body characteristics such as height, weight, facial features, tattoos, scars, etc., and similar crimes or activities, such as robbery or drunk driving.

The drones can also be launched from the vehicle and/or smart belt to be used for search and rescue missions, reconnaissance, surveillance purposes, etc.

In addition, the smart belt 10 worn by one person may be wired or wirelessly connected to other smart belts worn by other personnel to exchange data and information between smart belts based on proximity or other associative parameters pertaining to the wearer such as time of day, function performed, etc.

It should be noted that the phrase "wired or wirelessly connected to the smart belt 10" used herein means that a component is communicating with the microprocessor 12 and/or one or more other components/subsystems coupled or held in the smart belt 10 via a wired or wireless communication channel. It should also be noted that the sensors disposed within the holders of the smart belt 10 may be implemented by passive and/or active sensors depending on the desired application and functionality.

In addition, the headset, audio recording component or the video recording component may be operable to receive audible input commands from the wearer of the smart belt, the audible input being recognized and interpreted by a software component to allow for voice control of the smart belt or its externally or internally connected components, by the wearer of the smart belt.

The features of the present invention which are believed to be novel are set forth below with particularity in the appended claims. However, modifications, variations, and changes to the exemplary embodiments described above will be apparent to those skilled in the art, and the system and method described herein thus encompasses such modifications, variations, and changes and are not limited to the specific embodiments described herein.

What is claimed is:

1. A smart belt system to be worn by a person comprising:
an elongated belt;
a microprocessor coupled to the belt;
a bus disposed within the belt configured to conduct at least one of electricity and data for providing at least one of electricity and data to the microprocessor and at least one device electrically coupled to the bus:
a rechargeable power supply coupled to the belt and configured for providing electrical power to the microprocessor and the at least one device electrically coupled to the bus; and
at least one of an eyewear component, audio component, video component, and tactile component in wireless communication with the microprocessor and configured to relay information to the person via at least one of a visual display, audio sound, and tactile sensation related to an operating status of at least one of the rechargeable power supply and the at least one device.

2. The smart belt system of claim 1, further comprising an inductive power component coupled to the belt and configured to inductively charge the rechargeable power supply by inductive coupling when the wearer is sitting in a seat having an inductive power charging system.

3. The smart belt system of claim 1, further comprising:
a GPS component coupled to the belt and electrically coupled to the rechargeable power supply, the GPS component being configured to track the geo-location and movement of the belt;
logic instructions being executed by the microprocessor configured to monitor and regulate the activities of any device electrically coupled to the power bus and communicatively coupled to the microprocessor, the logic instructions further enable analysis of location and movement data generated by the GPS component;
a memory component configured for storing the logic instructions accessible by the microprocessor and disposed within the belt; and
a data storage component disposed within the belt and accessible by the microprocessor for storing activity data of any device in communication with the microprocessor and the location and movement data generated by the GPS component.

4. The smart belt system of claim 1, further comprising a wireless data communications system coupled to the belt and configured to wirelessly communicate with an external data communications system and the microprocessor.

5. The smart belt system of claim 1, further comprising:
logic instructions being executed by the microprocessor configured to monitor and regulate the activities of any device electrically coupled to the power bus and communicatively coupled to the microprocessor;
a memory configured for storing the logic instructions accessible by the microprocessor and disposed within the belt; and
a data storage component disposed within the belt and accessible by the microprocessor.

6. The smart belt system of claim 3, further comprising a plurality of audio sensors distributed on the person configured for generating audio signals in response to perceiving sounds of weapon fire, and transmitting the audio signals to the microprocessor for analysis, with data from the GPS component, to determine a probable location of the firing weapon.

7. The smart belt system of claim 4, further comprising clothing items worn by the user having special connectors enabling at least one of the microprocessor, wireless data communication system, GPS component, and data storage component to be communicatively coupled to the clothing items to enable transmission of a least one of data and electricity therebetween via conductive wires incorporated into the clothing items.

8. The smart belt system of claim 3, further comprising a network of distributed impact sensors incorporated into at least one clothing item worn by the person and configured to convert a strike on the at least one clothing item by a projectile to impact data representative of at least one of force, pressure, velocity, and direction of the projectile, and to transmit the data to the microprocessor for analysis, with data from the GPS component, to determine a probable point of origination of the projectile.

9. The smart belt system of claim 3, wherein at least one of a helmet, face shield, armored vest, uniform, and riot shield worn and carried by the person comprises a network of distributed impact sensors configured to convert a strike thereon by a projectile to data representative of at least one of force, pressure, velocity, and direction of the projectile, and to transmit the data to the microprocessor for analysis, with data from the GPS component, to determine a probable point of origination of the projectile.

10. The smart belt system of claim 4, further comprising a plurality of audio sensors distributed in the environment configured for generating audio signals in response to perceiving sounds of weapon fire, and transmitting the audio signals to the microprocessor for analysis, with data from the GPS component, to determine a probable location of the firing weapon.

11. The smart belt system of claim 4, further comprising a tracking device propelled from a dispenser, the dispenser being coupled to a structure located proximate to a road and configured to propel the tracking device onto a vehicle in response to the vehicle moving proximate to the dispenser, the tracking device further configured to relay GPS coordinates to at least one of the microprocessor and a graphical user interface for viewing by a person.

12. The smart belt system of claim 4, further comprising a drone in wireless communication with the wireless data communications system and configured to receive launch and navigation instructions, and the drone being configured to capture at least one of video images and GPS coordinates and to communicate the at least one of the captured video images and GPS coordinates to at least one of the microprocessor and a graphical user interface for viewing by a person.

13. The smart belt system of claim 4, further comprising a tracking device propelled from a dispenser, the dispenser being removably coupled to the belt.

14. The smart belt system of claim 6, wherein the microprocessor is further configured to generate a graphical map representation of the probable location of the firing weapon, and transmit the graphical map representation to a graphical user interface for display for viewing by a person.

15. The smart belt system of claim 8, wherein the microprocessor is further configured to generate a graphical map representation of the probable point of origination of the projectile, and transmit the graphical map representation to a graphical user interface for display for viewing by a person.

16. The smart belt system of claim 9, wherein the microprocessor is further configured to generate a graphical map representation of the probable point of origination of the projectile, and transmit the graphical map representation to a graphical user interface for display for viewing by a person.

17. The smart belt system of claim 11, wherein the tracking device comprises one of a transmitter configured to communicate location information, a radio-beacon transmitter or a dye.

18. The smart belt system of claim 12 wherein the drone is further configured to at least one of monitor and follow a tracking device coupled to a target.

19. The smart belt system of claim 12, further comprising an eyewear component displaying a summary of the status of the belt and at least one of the plurality of the devices associated with the belt, the eyewear component further configured to display a video feed from the drone.

20. The smart belt system of claim 18, wherein the microprocessor is configured to analyze at least one of the GPS coordinates and the captured video images, determine at least one address associated with at least one of the tracked individual and tracked vehicle in response to analyzing at least one of the GPS coordinates and the captured video images, and transmit the at least one of the address and identifying information associated with at least one of the tracked individual and tracked vehicle to at least one of the drone, a wearer of the belt, and a graphical user interface for viewing by a person.

21. The smart belt system of claim 18, wherein the microprocessor is configured to analyze at least one of the GPS coordinates and the captured video images, determine at least one of a possible identity of an individual being tracked, and a possible known residence address associated with the suspect being tracked in response to analyzing at least one of the GPS coordinates and the captured video images, and transmit at least one of an address and identifying information associated with at least one of the tracked individual and tracked vehicle to at least one of the drone and a wearer of the belt.

22. The smart belt system of claim 18, wherein the microprocessor is configured to transmit at least one of the GPS coordinates and the captured video images to a database to determine at least one address associated with at least one of the tracked individual and tracked vehicle being pursued in response to analyzing at least one of the GPS coordinates and the captured video images, and transmit the at least one of an address and identifying information to at least one of the drone and the wearer, the database being maintained on at least one of the storage component, a computing device associated with a vehicle communicatively coupled to at least one of the drone and the smart belt, and a remote computing device communicatively coupled to at least one of the drone and the smart belt.

23. The smart belt system of claim 12, wherein the drone is removably mounted to a mount located to at least one of an exterior of a vehicle, an interior of the vehicle, and the belt.

24. A smart belt system to be worn by a person comprising:
an elongated belt;
a microprocessor coupled to the belt;
a bus disposed within the belt configured to conduct at least one of electricity and data for providing at least one of electricity and data to the microprocessor and at least one device electrically coupled to the bus: and
an inductively rechargeable power supply coupled to the belt and configured for providing electrical power to the microprocessor and the at least one device electrically coupled to the bus, the rechargeable power supply being inductively rechargeable when the wearer is sitting in a seat having an inductive power charging system.

* * * * *